United States Patent [19]

Brisken

[11] Patent Number: 5,735,811
[45] Date of Patent: Apr. 7, 1998

[54] APPARATUS AND METHODS FOR ULTRASONICALLY ENHANCED FLUID DELIVERY

[75] Inventor: Axel F. Brisken, Fremont, Calif.

[73] Assignee: Pharmasonics, Inc., Mountain View, Calif.

[21] Appl. No.: 566,739

[22] Filed: Nov. 30, 1995

[51] Int. Cl.$^6$ .................................................. A61B 17/20
[52] U.S. Cl. ............................................. 604/22; 606/169
[58] Field of Search ........................... 606/169; 607/97; 604/22; 601/2; 310/26

[56] References Cited

U.S. PATENT DOCUMENTS

| | | | |
|---|---|---|---|
| 3,433,226 | 3/1969 | Boyd | 128/305 |
| 3,565,062 | 2/1971 | Kuris | 128/24 |
| 4,636,195 | 1/1987 | Wolinsky | 604/53 |
| 4,692,139 | 9/1987 | Stiles | 604/22 |
| 4,698,058 | 10/1987 | Greenfeld et al. | 604/266 |
| 4,808,153 | 2/1989 | Parisi | 604/22 |
| 4,838,853 | 6/1989 | Parisi . | |
| 4,870,953 | 10/1989 | DonMichael et al. | 128/24 |
| 4,936,281 | 6/1990 | Stasz | 128/660.03 |
| 4,948,587 | 8/1990 | Kost et al. | 424/435 |
| 5,085,662 | 2/1992 | Willard | 606/159 |
| 5,163,421 | 11/1992 | Bernstein et al. | 128/24.1 |
| 5,197,946 | 3/1993 | Tachibana | 604/22 |
| 5,267,954 | 12/1993 | Nita | 604/22 |
| 5,267,985 | 12/1993 | Shimada et al. | 604/290 |
| 5,269,291 | 12/1993 | Carter | 128/24 |
| 5,269,297 | 12/1993 | Weng et al. | 128/24 |
| 5,279,546 | 1/1994 | Mische et al. | 604/22 |
| 5,282,785 | 2/1994 | Shapland et al. | 604/21 |
| 5,286,254 | 2/1994 | Shapland et al. | 604/21 |
| 5,304,115 | 4/1994 | Pflueger et al. | 604/22 |
| 5,315,998 | 5/1994 | Tachibana et al. | 128/660 |
| 5,318,014 | 6/1994 | Carter | 601/2 |
| 5,324,255 | 6/1994 | Passafaro et al. | 604/22 |
| 5,342,292 | 8/1994 | Nita et al. | 604/22 |
| 5,344,395 | 9/1994 | Whalen et al. | 604/22 |
| 5,362,309 | 11/1994 | Carter | 604/22 |
| 5,380,273 | 1/1995 | Dubrul et al. | 604/22 |
| 5,397,301 | 3/1995 | Pflueger et al. | 604/22 |
| 5,447,509 | 9/1995 | Mills et al. | 606/1 |
| 5,456,259 | 10/1995 | Barlow et al. | 128/662.03 |
| 5,458,568 | 10/1995 | Racchini et al. | 604/19 |
| 5,458,631 | 10/1995 | Xavier | 607/117 |
| 5,462,523 | 10/1995 | Samson et al. | 604/30 |
| 5,465,725 | 11/1995 | Seyed-Bolorforosh | 128/662.03 |
| 5,474,530 | 12/1995 | Passafaro et al. | 604/22 |
| 5,474,531 | 12/1995 | Carter | 604/22 |

FOREIGN PATENT DOCUMENTS

| | | | |
|---|---|---|---|
| 0 189 329 | 7/1986 | European Pat. Off. | A61B 17/22 |
| 3-063041 | 3/1991 | Japan | A61B 17/22 |
| WO 90/01300 | 2/1990 | WIPO | A61B 17/32 |
| WO 91/19529 | 12/1991 | WIPO | A61M 29/02 |
| WO 94/05361 | 3/1994 | WIPO | A61M 25/00 |
| WO 95/22284 | 8/1995 | WIPO | A61B 8/12 |
| WO 95/24159 | 9/1995 | WIPO | A61B 17/36 |

OTHER PUBLICATIONS

Rosenchein, U. et al. "Experimental Ultrasonic Angioplasty: disruption of Atherosclerotic Plaques and Thrombi in Vitro and Arterial Recanalization in Vivo," (1990) JACC vol. 15, No. 3, pp. 711–717.

Yumita, N. et al. "Synergistic Effect of Ultrasound and Hematoporphyrin on Sarcoma 180," (1990) *Jpn. J. Cancer Res.* 81, pp. 304–308.

Tachibana, K. "Enhancement of Fibrinolysis with Ultrasound Energy," (1992) *J. Vascular & Interventional Radiography* 3(2) pp. 299–303.

*Primary Examiner*—Mark Bockelman
*Attorney, Agent, or Firm*—Townsend and Townsend and Crew LLP

[57] ABSTRACT

An ultrasonic catheter comprises a catheter body having an interface surface which extends at least partially over a circumferential portion of the catheter body. The interface surface is coupled to an oscillating driver so that axial and/or radial oscillations are radiated into a fluid environment surrounding the catheter body. Optionally, the catheter may be provided with a fluid infusion lumen and/or inflatable balloons on either side of the interface surface in order to deliver treatment fluid within a specific or isolated region in a body lumen.

53 Claims, 6 Drawing Sheets

APPARATUS AND METHODS FOR ULTRASONICALLY ENHANCED FLUID DELIVERY

BACKGROUND OF THE INVENTION

1. Field of the Invention

The present invention relates generally to medical devices and methods. More particularly, the present invention relates to apparatus and methods for the ultrasonically enhanced localized delivery of therapeutic fluids within the vasculature and other body lumens.

Despite the growing sophistication of medical technology, vascular (blood vessel) diseases, such as acute myocardial infarction (heart attack) and peripheral arterial thrombosis (blood clots in leg arteries), remain a frequent, costly, and very serious problem in health care. Current methods of treatment, often expensive, are not always effective. In the U.S. alone, the cost of treatment and support and the loss of productivity due to vascular diseases together exceed $40 billion per year.

The core of the problem is that diseased sites within the blood vessels narrow and eventually become completely blocked as a result of the deposition of fatty materials, cellular debris, calcium, and/or blood clots, thereby blocking the vital flow of blood. Current treatments include drugs, interventional devices, and/or bypass surgery. High doses of thrombolytics (clot-dissolving drugs) are frequently used in an effort to dissolve the blood clots. Even with such aggressive therapy, thrombolytics fail to restore blood flow in the affected vessel in about 30% of patients. In addition, these drugs can also dissolve beneficial clots or injure healthy tissue causing potentially fatal bleeding complications.

While a variety of interventional devices are available, including angioplasty, atherectomy, and laser ablation catheters, the use of such devices to remove obstructing deposits may leave behind a wound that heals by forming a scar. The scar itself may eventually become a serious obstruction in the blood vessel (a process known as restenosis). Also, diseased blood vessels being treated with interventional devices sometimes develop vasoconstriction (elastic recoil), a process by which spasms or abrupt reclosures of the vessel occur, thereby restricting the flow of blood and necessitating further intervention. Approximately 40% of treated patients require additional treatment for restenosis resulting from scar formation occurring over a relatively long period, typically 4 to 12 months, while approximately 1-in-20 patients require treatment for vasoconstriction, which typically occurs from 4 to 72 hours after the initial treatment.

Bypass surgery can redirect blood around the obstructed artery resulting in improved blood flow. However, the resulting bypass grafts can themselves develop scar tissue and new blood clots in five to ten years resulting in blockage and the need for further treatment. In summary, all current therapies have limited long term success.

The use of ultrasonic energy has been proposed both to mechanically disrupt clot and to enhance the intravascular delivery of drugs to dissolve clot and inhibit restenosis. Ultrasonic energy may be delivered intravascularly using specialized catheters having an ultrasonically vibrating surface at or near their distal ends. One type of ultrasonic catheter employs a wire or other axial transmission element to deliver energy from an ultrasonic energy vibration source located outside the patient, through the catheter, and to the ultrasonically vibrating surface. While such systems can deliver relatively large amounts of energy, the need to transmit that energy through the entire length of the catheter presents a substantial risk to the patient.

Moreover, such catheters are typically rigid and cannot easily traverse narrow, tortuous arteries, such as the coronary arteries which frequently need to be treated. Because of their rigidity and inability to follow the vascular lumen, these catheters present a serious risk of vascular wall perforation.

In order to avoid the use of ultrasonic transmission members, catheters having ultrasonic transducers mounted directly on their distal ends have also been proposed. See, for example, U.S. Pat. Nos. 5,362,309; 5,318,014; 5,315,998; 5,269,291; and 5,197,946. By providing the transducer within the catheter itself, there is no need to employ a transmission element along the entire length of the catheter. While such catheter designs offer enhanced safety, they suffer from a limited ability to generate large amounts of ultrasonic energy. Even though certain of these designs, such as that described in U.S. Pat. No. 5,362,309, employ "amplifiers" which enhance the delivery of ultrasonic energy, such designs are still problematic. In particular, the catheters of the '309 patent have relatively long, rigid transducers and are not amenable to receiving guidewires, both of which features make it difficult to position the catheters within the vasculature, particularly the coronary vasculature.

Of particular interest to the present invention, the use of ultrasonic energy to enhance the localized intraluminal delivery of drugs and other therapeutic agents has been proposed. For example, the intravascular delivery of fibrinolytic and anti-thrombogenic agents for the primary treatment of clot and post-angioplasty treatment of intravascular sites has been proposed in a number of the above-listed patents. Generally, the catheters used for ultrasonically enhanced fluid delivery are provided with an acoustic element, e.g., an ultrasonic transducer or ultrasonic transmission element, a drug infusion lumen, and a radiating surface disposed to impart ultrasonic energy into fluid infused from the catheter. While holding great promise, such catheters have suffered from several major limitations. First, the acoustic elements were generally too large in diameter and/or too rigid over too great a length to permit delivery through tortuous arteries, such as the coronary arteries which are particularly prone to suffering vascular disease. Second, the acoustic elements have typically been able to provide only limited ultrasonic displacement. Finally, the ultrasonic displacements were typically limited to forwardly projected longitudinal waves without providing significant "shearing" waves (radially emanating transverse waves) which might be more suitable for opening pores in tissue structures to enhance penetration of pharmacological molecules.

For these reasons, it would be desirable to provide improved ultrasonic catheter designs overcoming at least some of the problems discussed above. In particular, it would be desirable to provide ultrasonic catheters having both ultrasonic transducers and drug delivery capabilities where the transducer designs are optimized for interaction with drugs released into an intraluminal environment, particularly an intravascular environment. For example, it would be desirable if the catheters included interface surfaces for imparting ultrasonic energy into the fluid environment surrounding the catheter, where the surfaces were relatively large, usually being greater than about 10 mm$^2$, preferably being greater than about 30 mm$^2$. It would be further desirable if the interface surfaces were generally cylindrical, surrounding at least a portion of the catheter body near its distal end and providing for axially isotropic radiation of ultrasonic energy from the catheter. It would also be desirable to provide interface surfaces capable of moving parallel to the longitudinal axis of the catheter in order to impart a transverse (shear) wave into the fluid environment surrounding the catheter and onto the vessel wall surface. The amplitude of displacement of the interface surface should impart sufficient shearing of the fluid environment to allow enhanced penetration of pharmacological molecules into the vascular wall, and in particular should not be substantially or totally attenuated before reaching the vascular wall. It would be still further desirable if the interface surfaces, in addition to a cylindrical surface area, included forwardly disposed surface regions capable of radiating ultrasonic energy in the forward direction from the catheter. It would be still further desirable to provide methods for the simultaneous intraluminal delivery of ultrasonic energy and fluid agents, where the ultrasonic energy has been adapted to induce wave motion in fluid adjacent to a surface of the catheter. The use of such catheters and apparatus, however, should not be limited to the enhanced delivery of fluid agents and in at least some cases should be able to provide for the direct stimulation of the vascular wall or stenotic regions within the vascular lumen without the simultaneous delivery of fluid agents.

2. Description of the Background Art

Catheters having ultrasonic elements with the capability of delivering thrombolytic and other liquid agents are described in U.S. Pat. Nos. 5,362,309; 5,318,014; 5,315,998; 5,197,946; 5,397,301; 5,380,273; 5,344,395; 5,342,292; 5,324,255; 5,304,115; 5,279,546; 5,269,297; 5,267,954; 4,870,953; 4,808,153; 4,692,139; and 3,565,062; in WO 90/01300; and in Tachibana (1992) JVIR 3:299–303. A rigid ultrasonic probe intended for treating vascular plaque and having fluid delivery means is described in U.S. Pat. No. 3,433,226. An ultrasonic transmission wire intended for intravascular treatment is described in U.S. Pat. No. 5,163,421 and Rosenschein et al. (1990) JACC 15:711–717. Ultrasonically assisted atherectomy catheters are described in U.S. Pat. No. 5,085,662 and EP 189329. Ultrasonic enhancement of systemic and localized drug delivery is described in U.S. Pat. Nos. 5,286,254; 5,282,785; 5,267,985; and 4,948,587; in WO 94/05361 and WO 91/19529; in JP 3-63041; and in Yumita et al. (1990) JPN. J. CANCER RES. 81:304–308. An electrosurgical angioplasty catheter having ultrasonic enhancement is described in U.S. Pat. No. 4,936,281. An infusion and drainage catheter having an ultrasonic cleaning mechanism is described in U.S. Pat. No. 4,698,058. A drug delivery catheter having a pair of spaced-apart balloons to produce an isolated region around arterial plaque is described in U.S. Pat. No. 4,636,195.

SUMMARY OF THE INVENTION

According to the present invention, a catheter for the intraluminal delivery of ultrasonic energy comprises a catheter body having a proximal end and a distal end. An oscillating driver is disposed in the catheter body, and an interface member having an interface surface is coupled to the oscillating driver. The interface surface extends axially over at least a portion of a circumferential surface of the catheter body, usually being cylindrical, and axial and/or radial oscillations of the interface surface induce wave motion in fluid lying adjacent to the catheter body. While particularly intended for enhancing the mixing and absorption of therapeutic fluid agents delivered to a luminal target site, the catheters of the present invention would also be useful for the direct delivery of ultrasonic energy into the body lumen, particularly by engaging the circumferential interface surface directly against the target site.

The interface surface may further include a portion which extends laterally over a distal end of the catheter, where the lateral surface can be flat, concave, convex, or have an irregular geometry selected to radiate ultrasonic energy in a desired pattern. The oscillating driver will usually be connected to the interface member to induce longitudinal oscillations therein. In such cases, the circumferential surface of the interface member will induce a wave motion in a direction parallel to the axis of the catheter body while the forward lateral surface (if present) will induce waves in a distal direction away from the distal end of the catheter body. Alternatively, the oscillating driver may be selected to radially oscillate an interface surface, usually a cylindrical interface surface, to induce a radial wave pattern extending outwardly from the catheter body.

The catheters of the present invention will usually further comprise a lumen for delivering a fluid agent from a proximal end of the catheter body to a location near the interface member. The lumen may be formed within the catheter body itself. Alternatively, an annular lumen may be provided by disposing a sheath coaxially about the catheter body. The catheters of the present invention, however, could also be employed with drugs and other liquid agents delivered by other apparatus, such as separate fluid infusion catheters, other drug release devices and prostheses (such as drug delivery stents), systemic administration (for example where the drugs are activated or enhanced by the localized ultrasonic delivery), or the like.

In a first particular embodiment of the catheter of the present invention, the oscillating driver is a longitudinally oscillating driver mounted to extend distally from the distal end of the catheter body. The interface member is coupled to the distal end of the longitudinally oscillating driver and includes an interface surface having a portion which is disposed circumferentially about the catheter body, more usually being a cylindrical surface. Usually, the interface surface will include both the circumferential portion and a lateral portion, such as a forwardly disposed surface, which may be flat, convex, concave, or irregular. The longitudinally oscillating driver may optionally be a resonant driver comprising a spring element which connects the interface member to the catheter body. The spring element, the mass of the interface member, and the frequency and other operational characteristics of the driver (including its mass) will be selected to operate resonantly. The longitudinally oscillating driver may comprise any conventional longitudinally oscillating ultrasonic transducer, such as a tubular piezoelectric transducer, a piezoelectric stack, or the like. The driver can also be a magnetostrictive driver. Optionally, the catheter will further comprise a pair of expansible members disposed proximally and distally of the interface surface, where the expansible members can selectively isolate a region about the interface surface in order to contain a therapeutic fluid therein, while ultrasonic energy is being delivered.

In a second specific embodiment, the catheter comprises a catheter body and interface member generally as described above. The interface member is driven by a pair of longitudinally oscillating drivers connected in tandem so that the combined lengths of the drivers remain substantially constant as the drivers are oscillated. The interface member is mechanically coupled to the catheter body through the pair of drivers so that simultaneous oscillation of the drivers induces longitudinal movement of the interface surface relative to the catheter body. A distal end of the distal-most driver and a proximal end of the proximal-most driver may be fixed relative to the catheter body, and the interface member secured to a location between the drivers. In this way, the interface member will float relative to the anchored ends of the drivers and be driven by the free ends of the drivers. Alternatively, the inner ends of the drivers may be fixed relative to the catheter body, and the interface member may be secured to the distal end of the distal-most driver and the proximal end of the proximal-most driver. In this way the outer ends of the drivers support and drive the interface member. In both these embodiments the interface surfaces are generally cylindrical, usually having a length in the range from 6 mm to 30 mm and a diameter in the range from 2 mm to 5 mm. The cylindrical interface surface may be smooth, or optionally may be irregular in order to enhance fluid coupling to the surface as it is axially oscillated.

In a third specific embodiment, the interface member may comprise an annular flange that is disposed circumferentially about the catheter body. Usually, the flange will be driven by a pair of longitudinally oscillating drivers as described above. Optionally, the catheter will further comprise a pair of expansible memebers disposed proximally and distally of the interface surface, where the expansible members can selectively isolate a region about the interface surface in order to contain a therapeutic fluid therein, while ultrasonic energy is being delivered.

According to the method of the present invention, a catheter is provided having an interface member near its distal end. A circumferential interface surface of the interface member is advanced to a region near an intraluminal site to be treated. The interface surface is driven to induce wave motion in fluid adjacent to the circumferential surface. Usually, the interface surface will be oscillated in an axial direction in order to induce wave motion in the axial direction relative to the catheter body. Alternatively, the circumferential interface surface may be radially oscillated in order to induce radial wave motion emanating from the interface surface. The method is particularly useful for treating intraluminal lesions, such as a vascular treatment site following angioplasty. An interface member is driven at a desired ultrasonic frequency, usually in the range from about 10 kHz to 300 kHz. The application of ultrasonic energy enhances the activity and luminal wall penetration of certain treatment agents, including fibrinolytic and anti-thrombotic treatment agents.

DESCRIPTION OF THE SPECIFIC EMBODIMENTS

The present invention provides apparatus and methods for the treatment of luminal conditions, particularly for the treatment of diseases of the coronary and peripheral vasculature. Specific conditions include coronary and peripheral arterial disease and thrombosis. The apparatus and methods are useful for primary treatment of such diseases, where the purpose is to ablate, dissolve, or otherwise disrupt the clot, plaque, or other stenotic lesions which are responsible for the disease. For example, catheters constructed according to the principles of the present invention can be used to directly engage and transmit ultrasonic energy into the stenotic material in order to mechanically disrupt the material to open the associated blood vessel lumen. Such mechanical disruption can be accomplished with or without the simultaneous administration of pharmacologic and therapeutic agents. The apparatus and methods of the present invention are also useful to enhance the administration of therapeutic agents, where the therapeutic agents are primarily responsible for the disruption of the stenotic material. Such cases, the catheter may be engaged against the stenotic material, or alternatively may be maintained a short distance away from the stenotic material. The ultrasonic energy will be relied on to agitate and promote the penetration of the therapeutic agent into the stenotic material. Suitable therapeutic agents include known thrombolytic and fibrinolytic drugs, such as heparin, tissue plasminogen activator (tPA), urokinase, streptokinase, and the like. The catheters and methods of the present invention are still further useful for the treatment of vascular sites which have been previously treated by other interventional techniques, such as angioplasty, atherectomy, laser ablation, and the like. In such cases, the catheters will be used to agitate and promote the penetration of anti-thrombogenic agents into the vascular or other luminal wall to inhibit restenosis. Suitable anti-thrombogenic agents include hirudin, hirulog, heparin, tPA, urokinase, streptokinase, and the like. In addition to treatment of the vascular system, the present invention may also be used for systemic and localized delivery of drugs within other body lumens, such as the ureter, the urethra, fallopian tubes, and the like. The present invention may further be used for the systemic and localized delivery of drugs within the vascular system for treatment of non-vascular diseases, e.g., for the treatment of tumors by the localized delivery of drugs to the vasculature supporting the tumor.

The catheter of the present invention will comprise a catheter body having a proximal end and distal end. The catheter body will have dimensions and physical characteristics selected for the particular use. For vascular applications, the length of the catheter body will typically be from 50 cm to 200 cm, usually being from 75 cm to 150 cm, and the diameter will be from 1 mm to 5 mm, usually being from 2 mm to 4 mm. The diameter of the catheter body may vary over its length, and different portions of the length may be formed from different materials. In the exemplary embodiment, the catheter body will comprise a single extrusion having at least one lumen therethrough. The lumen will usually be capable of receiving a guidewire, and may also be capable of delivering therapeutic agents and/or carrying electrical wires for connection from the proximal end of the catheter body to the distal end. Alternatively, the catheter body may include separate lumens for delivering therapeutic agent(s), routing electrical wires for connection to the ultrasonic transducer, or other purposes. The catheter body may be reinforced over all or a portion of its length. Conventional reinforcement materials include wire braids, wire meshes, wire coils, and the like. When employed with a guidewire for placement within the vasculature, the catheter body may have an "over-the-wire" design or a "rapid exchange" design. In the former case, the guidewire lumen will extend substantially through the entire length of the catheter body. In the latter case, the guidewire lumen will terminate in a proximal guidewire port located relatively near the distal end of the catheter body, usually within 50 cm, more usually within 30 cm, and often within 25 cm or less. Usually, a proximal housing will be secured to the proximal end of the catheter body, where the housing includes a guidewire port, a therapeutic agent infusion port, and the like.

An interface member will be provided on the catheter body for radiating energy, typically ultrasonic energy, into an environment surrounding the catheter body. The interface member will include an interface surface where at least a portion of the surface is disposed circumferentially about the catheter body. The circumferential portion will usually be a cylinder, and the interface member and surface may be oscillated axially (i.e., back and forth generally in the direction of the catheter body), radially (i.e., in a radial direction relative to the axis of the catheter body), or in a combination of both axial and radial directions. In either case, the energy will radiate away from the cylindrical surface of the interface member in a generally uniform pattern, i.e., isotropically (radially outward). Such uniform radiation is particularly advantageous for enhancing the penetration of therapeutic agents into a length of an intraluminal wall adjacent the cylindrical surface.

In the exemplary embodiments, the cylindrical interface surface will typically have a length in the range from 6 mm to 30 mm, preferably from 8 mm to 15 mm. The outer diameter of the cylindrical surface will typically be in the range from 2 mm to 5 mm, more usually from 3 mm to 4 mm. The interface member may further include a forwardly disposed lateral surface, typically being formed laterally at the distal end of the cylindrical surface. The lateral surface may itself be flat, convex (in the form of a forwardly disposed dome at the distal end of the cylindrical surface), concave, or irregular. The cylindrical surface and/or the forwardly disposed lateral surface may also have surface irregularities formed therein. For example, a plurality of ridges, protrusions, or the like, may be provided for enhancing the transfer of oscillatory motion into the fluid adjacent the surface.

A driver will be provided on the catheter body for oscillating the interface member in a desired manner. Usually, the driver will be separate from the interface member. In some cases, however, it may be possible to provide an oscillatory driver which also defines the interface surface, particularly for radially oscillating drivers as described in more detail hereinafter. The drivers will usually be ultrasonic transducers, including tubular piezoelectric transducers, piezoelectric stack transducers, magnetostrictive drivers, or the like. Optionally, the drivers may be incorporated in a resonant drive assembly, typically including a spring element attaching the interface member to the catheter body, where the ultrasonic driver is a longitudinally oscillating driver disposed between the catheter body and the interface member. Longitudinally oscillating drivers will usually be selected to oscillate with an amplitude in the range from 0.05 µm to 20 µm, preferably from 0.5 µm to 2 µm. The details of such drivers and resonant drive assemblies are set forth in copending application Ser. No. 08/565,575 (Attorney Docket No. 17148-000200) filed Nov. 30, 1995 now U.S. Pat. No. 5,725,494 assigned to the assignee of the present application, the full disclosure of which is incorporated herein by reference.

The catheters of the present invention may further comprise expansible members disposed proximally and distally of the interface surface of the interface member. The expansible members, typically inflatable elastomeric balloons, may be utilized to engage a luminal wall to isolate a luminal region to be treated.

Figure 1:
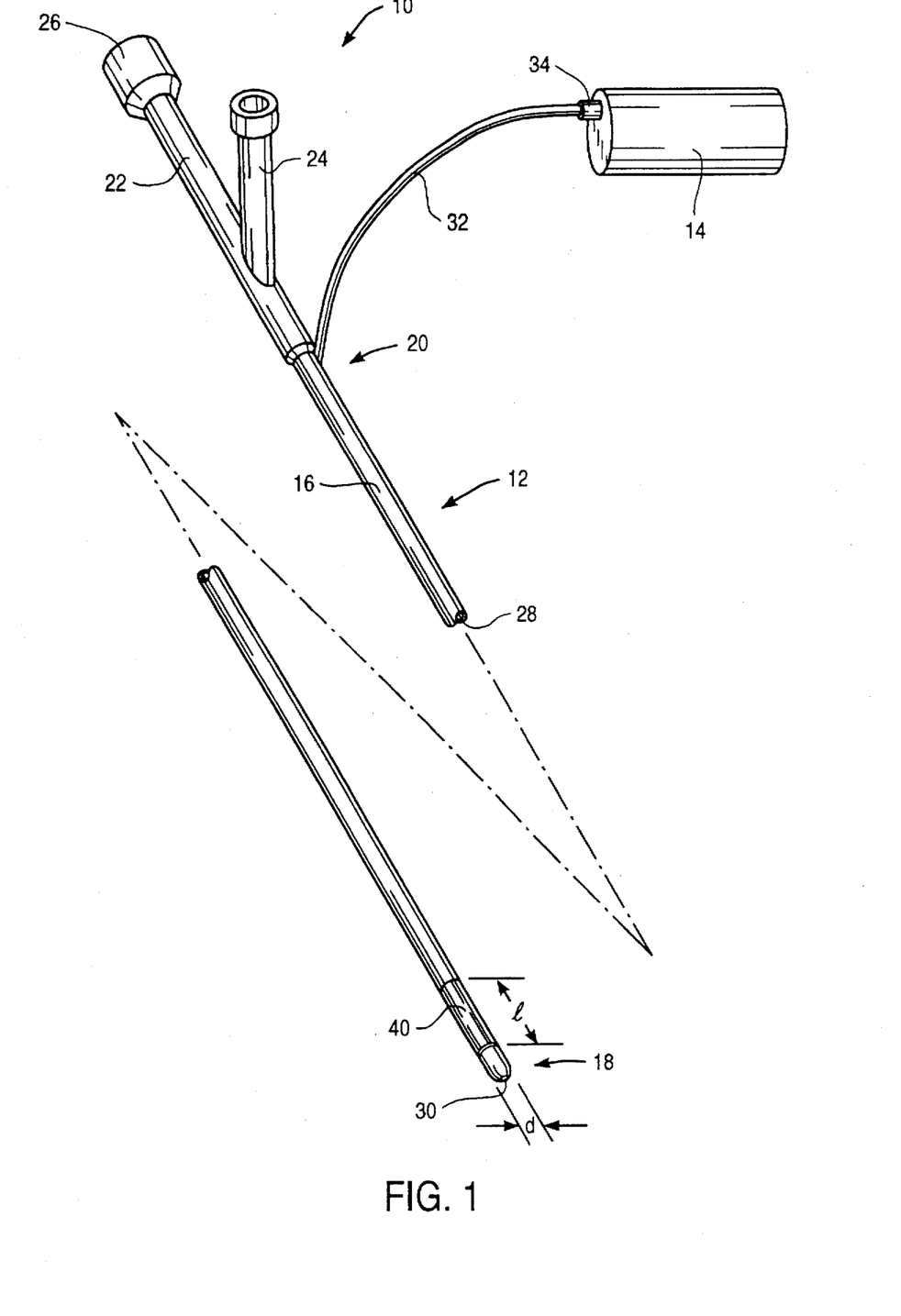
FIG. 1 illustrates an exemplary catheter and ultrasonic energy source constructed in accordance with the principles of the present invention.

Referring now to FIG. 1, a catheter system 10 comprising a catheter 12 constructed in accordance with the principles of the present invention and an ultrasonic power supply 14 is illustrated. The catheter 12 includes a catheter body 16 having a distal end 18 and a proximal end 20, a proximal housing 22 having a fluid infusion port 24, and a guidewire port 26. The catheter 12 includes at least a single lumen 28 extending from the proximal end 20 to the distal end 18 and connected to both the fluid infusion port 24 and the guidewire port 26. A cable 30 extends from the proximal end 20 of the catheter body 16 (typically through the lumen 28) and includes a connector 32 which may be removably attached to the power supply 14. The power supply 14 will be selected to drive the ultrasonic transducer (described below) at about a preselected frequency. The power supply 14 will typically comprise a conventional signal generator, such as those that are commercially available from suppliers such as Hewlett-Packard, Palo Alto, Calif., and Tektronics, Portland, Oreg., and a power amplifier, such as those commercially available from suppliers such as ENI Rochester, N.Y. and Krohn-Hite, Avon, Mass. Alternatively, the power supply may comprise custom signal generator and power amplifier circuits with tracking circuits to keep the driving frequency at the resonant frequency of the ultrasonic driver in the catheter tip as this resonant frequency drifts due to thermally induced material variations.

The catheter 12 includes an interface surface 40 disposed circumferentially about a portion of the catheter body 16. As shown in FIG. 1, the interface surface 40 is cylindrical and extends fully about the catheter body over a length l. The length l and outer diameter d of the cylindrical interface surface 40 will usually be within the ranges set forth above. It will be appreciated that the interface surface need not extend fully about the catheter body and in some cases could form a three-quarters cylindrical surface, a one-half cylindrical surface, or the like. The interface surface of the present invention, however, will extend in the axial direction over the circumferential surface of the catheter body for a minimum distance, again within the ranges set forth above.

Figure 2:
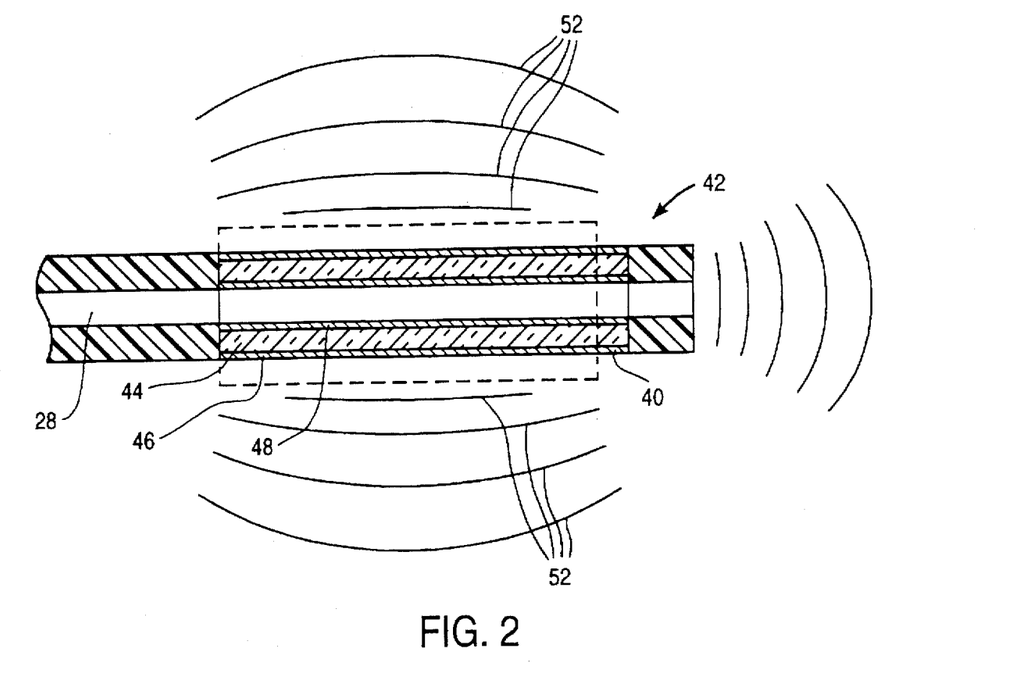
FIG. 2 is a detailed view of the distal end of the catheter of FIG. 1, shown in cross-section.
Figures 3, 4:
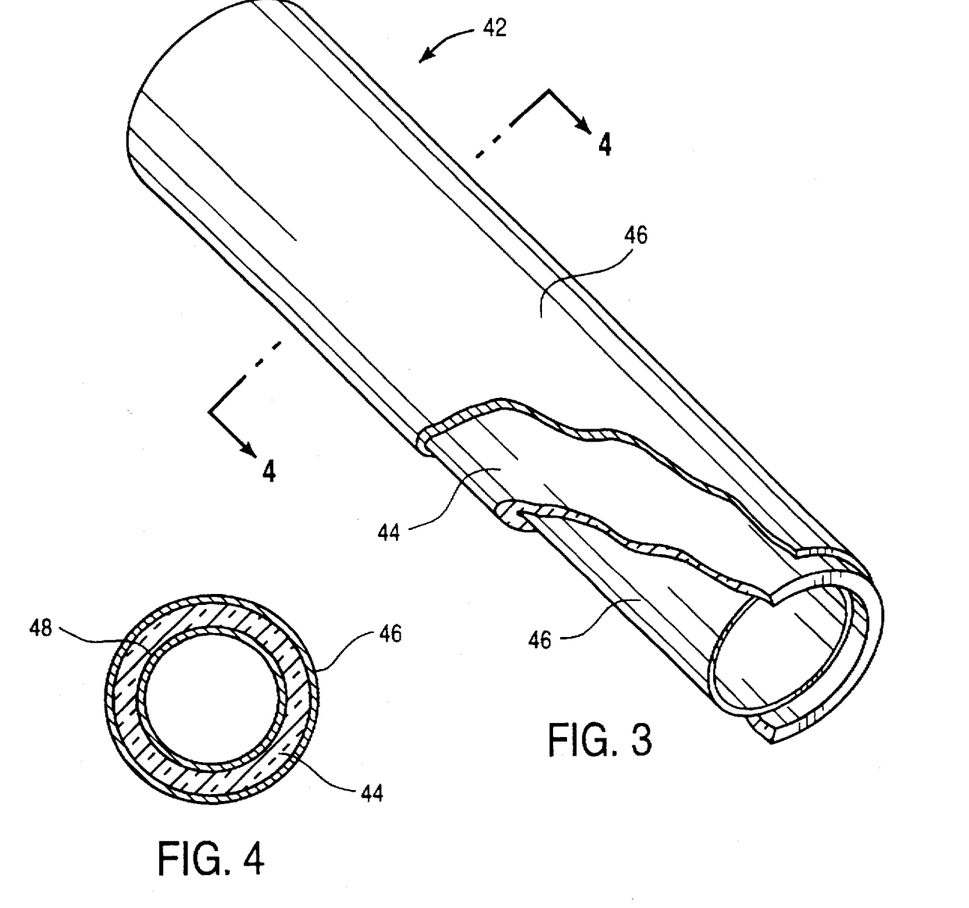
FIG. 3 is a perspective view of the tubular piezoelectric transducer which is incorporated in the catheter of FIG. 1, with portions broken away.
FIG. 4 is a cross-sectional view taken along line 4—4 of FIG. 3.

Referring now to FIGS. 2–4, the construction of an oscillating driver assembly 42 comprising the interface surface 40 is illustrated in detail. The oscillating driver 42 comprises a tubular piezoelectric ceramic 44 sandwiched between an outer electrode 46 and an inner electrode 48. Application of a suitable driving voltage to the electrodes 46 and 48 will cause the tubular piezoelectric transducer 52 to oscillate both longitudinally, radially, and in thickness. A suitable driving voltage will be from 10 V to 200 V. The resultant radial and axial displacements are best observed in FIG. 2, where a radial displacement in the range from 0.005 µm to 0.3 µm and an axial displacement in the range from 0.04 µm to 2 µm, may be achieved under non-resonant conditions. Under resonant conditions (i.e., where the oscillating driver assembly includes components of a resonant system so that the interface surface is resonantly oscillated) longitudinal displacement can be much greater, typically up to 20 µm and above.

Figure 9:
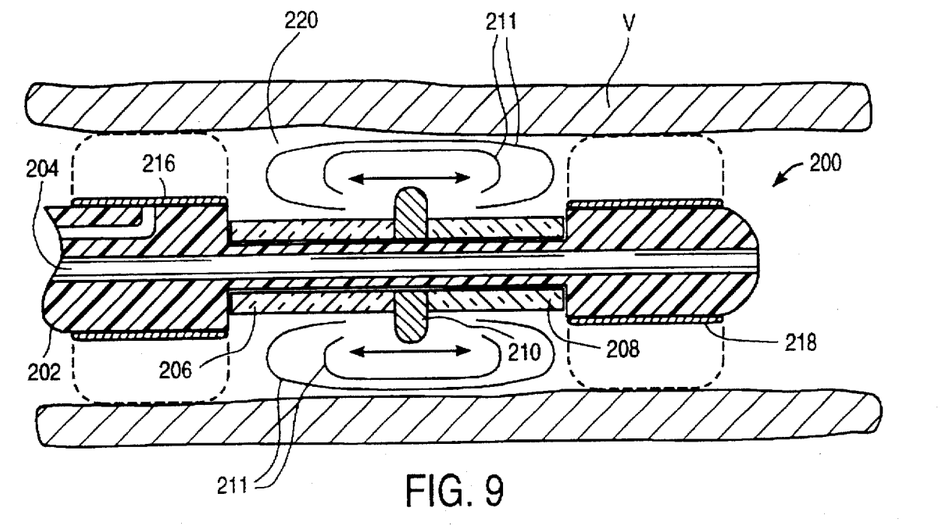
FIG. 9 is a detailed view of the distal end of still yet another catheter constructed in accordance with the principles of the present invention, shown in cross-section within a blood vessel.

The embodiment of FIG. 2 is preferably employed in combination with a pair of spaced-apart isolation balloons or other isolating members (as illustrated in FIG. 9). Such isolation balloons can form an isolated treatment volume surrounding the distal end of the catheter, and the presence of the lateral interface surface 40 is particularly useful since it can transfer oscillatory motion directly into this isolated fluid environment. In such cases, it will be desirable to provide one or more perfusion ports from the central lumen 28 in order to deliver fluid into the isolated region.

The oscillating driver assembly 42 provides both the oscillating driver and the interface member/surface of the present invention. The oscillating driver may be in the form of a tubular transducer including a piezoelectric tube 44 formed from a suitable material, as described above, sandwiched between an outer electrode 46 and inner electrode 48. Application of a suitable driving voltage to the electrodes 46 and 48 will cause the tubular transducer to oscillate both longitudinally and radially. A suitable driving voltage will be from 10 V to 200 V. The resulting axial displacement is shown in broken line in FIG. 2, where displacements in the range from 0.05 µm to 20 µm, usually from 0.5 µm to 2 µm, may be achieved.

As illustrated in FIGS. 2–5, the driver is not incorporated into the preferred embodiment of a resonant system. The driver could readily be converted into a resonant system by incorporating the spring member of copending application Ser. No. 08/565,575 filed Nov. 30, 1995 (Attorney Docket No. 17148-000200) now U.S. Pat. No. 5,725,494, the full disclosure of which has previously been incorporated herein by reference. The transducer assembly 42 generates wave motion in the form of wave fronts 52 which propagate radially outward from the cylindrical surface 40. Although not illustrated in FIG. 1, the catheter 12 could readily incorporate isolation balloons on the distal and proximal sides of the interface surface 40. The inclusion of isolation balloons is described in detail in connection with the embodiment of FIG. 9 below.

Figure 5:
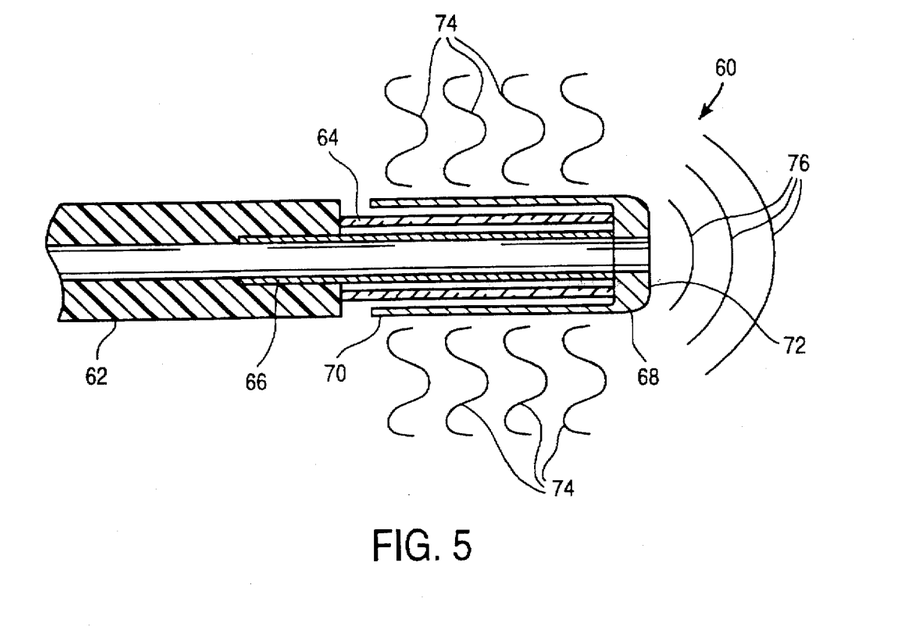
FIG. 5 is a detailed view of the distal end of a preferred embodiment of the catheter of the present invention, wherein the interface member incorporates both a circumferential surface and a forwardly disposed surface.

Referring now to FIG. 5, a preferred ultrasonic transducer assembly 60 is illustrated at the end of a catheter body 62. The catheter body 62 will be generally the same as catheter body 12 illustrated in FIG. 1. The transducer assembly 60 comprises a tubular piezoelectric transducer 64, (electrodes not shown) a spring member 66 extending distally from the distal end of catheter body 62, and an interface member 68 attached to the distal end of the spring member 66 and the transducer 64. The distal end of the catheter 62 shall provide a rigid anchoring of the proximal ends of the spring element 66 and the tubular piezoelectric transducer 64, where the effective mass of the distal catheter end shall be many times the mass of the interface member 68. Alternatively, a tail mass (not shown) may be located between the distal end of the catheter and the proximal ends of the spring element and the transducer element, where the mass of the tail mass is at least four times the mass of the interface member, preferably more than eight times the mass of the interface member. The interface member 68 has both a cylindrical interface surface 70 and a forwardly disposed interface surface 72. Longitudinal oscillation of the interface member 68 thus provides for the propagation of waves in two general directions. First, the cylindrical surface 70 produces transversely oscillating "shear" waves which radiate radially from the catheter, as illustrated by wavefront lines 74. The forward interface surface 72, in turn, propagates longitudinal waves in the distal direction, as illustrated by wavefront lines 76.

Preferably, the ultrasonic transducer assembly 60 will be a resonant system, where the elastic modulus of spring member 66 and of the transducer 64, and mass of interface member 68 are selected to provide for resonant operation at a particular frequency. Optionally, a tail mass (not shown) can be secured at the proximal end of the transducer 64, where the tail mass has significantly greater mass than the mass of the interface member 68. The tail mass, however, will not always be necessary, and in many cases the catheter body 62 will provide sufficient anchoring for operation of the transducer assembly 60 in a resonant manner. The mass of the interface member 70 will usually be in the range from 0.3 gm to 4 gm, more usually from 0.5 gm to 2 gm.

Figure 6:
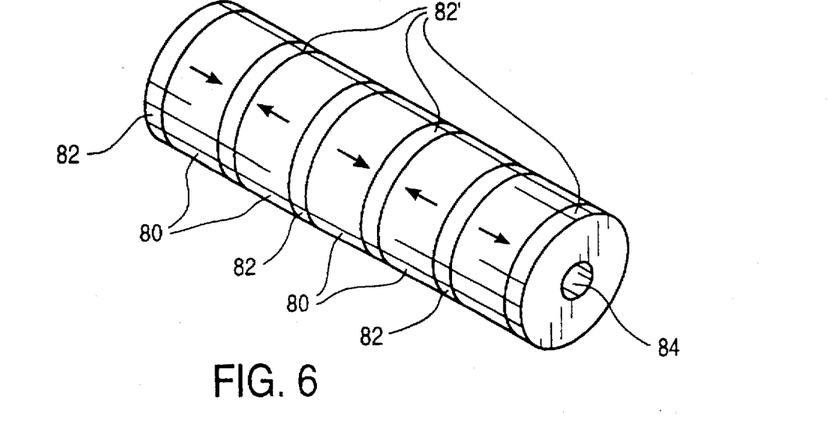
FIG. 6 is a perspective view of a piezoelectric stack transducer which could be used in the catheter of FIG. 1.

The ultrasonic transducer 64 may be a tubular transducer, as previously described in connection with FIG. 2, or alternatively may be a piezoelectric stack transducer comprising a plurality of piezoelectric disks 80 stacked with alternating polarity and with electrode plates 82 and 82', as illustrated in FIG. 6. Positive electrodes 82 will be connected to the positive terminal and negative electrodes 82' will be connected to the ground terminal of the power supply 14 in order to induce longitudinal vibrations in the piezoelectric stack. The arrows shown in FIG. 6 on the ceramic layers of the piezoelectric stack indicate the orientation of the polarity of each layer. Typically, the piezoelectric stack will be attached to a power supply comprising a sine wave generator, usually where the sine wave is biased above ground. The stack may be machined to include a lumen 84 to accommodate the spring member 66, as illustrated in FIG. 5. The ultrasonic transducer 64 could also be replaced by a magnetostrictive driver as described in more detail in copending application Ser. No. 08/566,740 filed Nov. 30, 1995 (Attorney Docket No. 17148-000500) now U.S. Pat. No. 5,728,062, the full disclosure of which is incorporated herein by reference.

The spring element which joins the interface member to the tail mass may comprise a single component, e.g., a single solid rod or hollow tube disposed along the longitudinal axis of the catheter or a cylindrical shell either within or external to the longitudinally oscillating driver. Alternatively, the spring element may comprise a plurality of components, such as a plurality of rods or tubes disposed symmetrically about the longitudinal axis of the catheter. The spring element may be composed of any of a wide variety of materials, most typically being a stainless steel, such as a hardened stainless steel having a Rockwell stiffness of at least about 35. The cross-sectional area of the spring element (s) shall be sufficient to provide a maximum tension of approximately 20% of the tensile strength of the material, typically about 25,000 PSI, at the time when the spring experiences its maximum deformation, i.e., the time of maximum forward displacement of the interface member. The assembly of the tail mass, interface member, and longitudinally oscillating driver is compressed by the spring mass with a static force sufficient to present continuing compressive forces at the time when the assembly shrinks to its minimum longitudinal displacement. The interface member and spring mass shall have a mass and stiffness which together assure that the spring element retains compressive force on the interface member at the time of maximum reverse acceleration in order to prevent the interface mass from separating from the driver element. The time of maximum reverse acceleration occurs at the time of maximum forward displacement.

Figure 7:
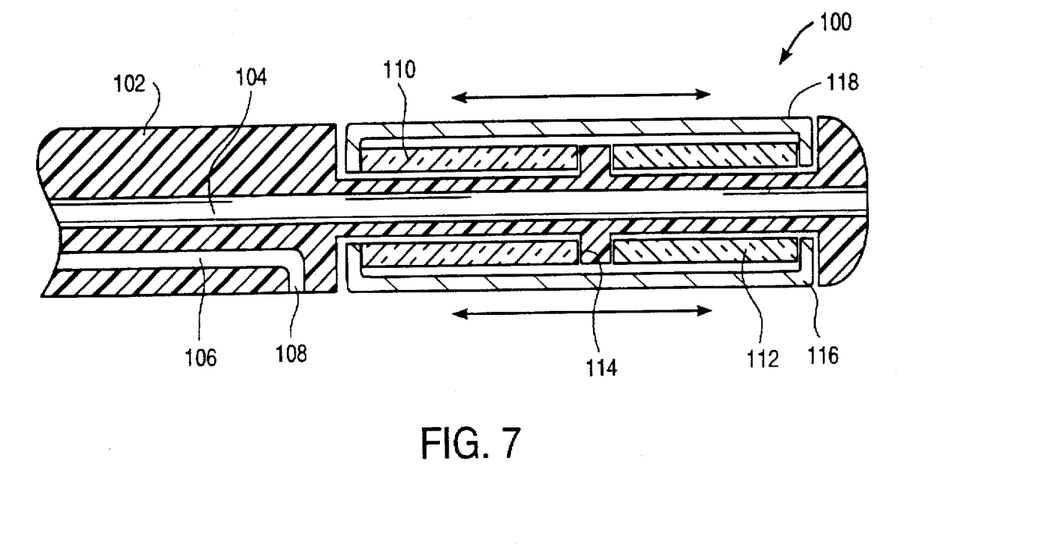
FIG. 7 is a detailed view of the distal end of another embodiment of the catheter constructed in accordance with the principles of the present invention, shown in cross-section.

Referring now to FIG. 7, another embodiment of an ultrasonic transducer assembly 100 constructed in accordance with the principles of the present invention is illustrated. The transducer assembly 100 is mounted at the end of a catheter body 102 having a central lumen 104 for receiving a guidewire and a second lumen 106 for receiving fluid infusate. A discharge port 108 of lumen 106 is disposed near the transducer assembly 100 so that a therapeutic agent can be delivered in the immediate region of the transducer. Although not illustrated, the catheter 102 could be modified to include isolation balloons, as described in more detail below.

The transducer assembly 100 comprises a first tubular transducer 110 and a second tubular transducer 112 disposed on the proximal and distal sides of flange 114 which is fixed relative to the catheter body 102. The transducers 110 and 112 may be tubular piezoelectric transducers, piezoelectric stack transducers, magnetostrictive drivers, or the like. In all cases, the transducers 110 and 112 will be wired so they oscillate longitudinally in the same direction, but 180° out of phase. In this way, the total distance between the proximal end of transducer 110 and the distal end of transducer 112 will remain constant, while the ends displace axially in a synchronous manner. An interface member 116 having cylindrical interface surface 118 is attached to the respective ends of the first transducer 110 and second transducer 112. In this way, the transducers will be driven in a longitudinally oscillating manner at a frequency determined by the characteristics of the transducers.

Figure 8:
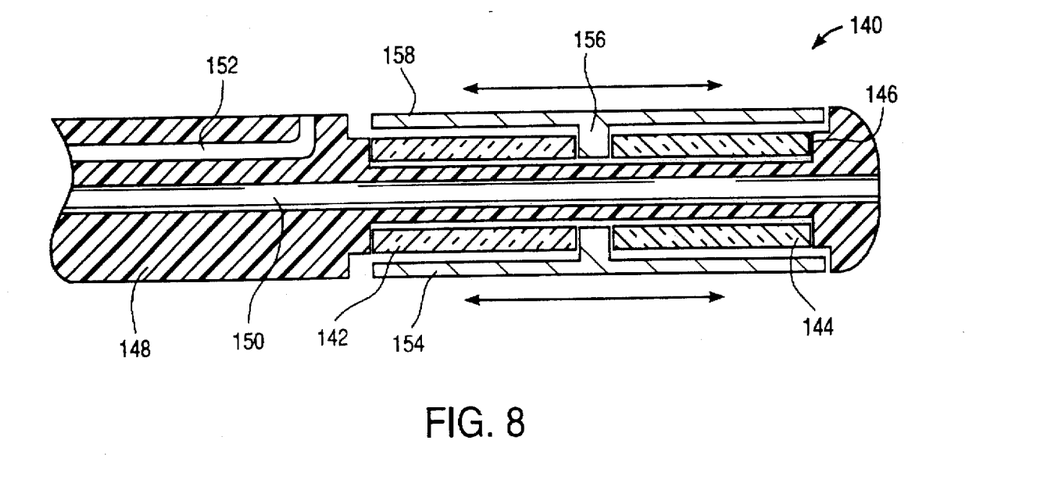
FIG. 8 is a detailed view of the distal end of yet another catheter constructed in accordance with the principles of the present invention, shown in cross-section.

In the transducer assembly 100 the inner ends of the transducers 110 and 112 are fixed to the catheter body 102 by means of the flange 114. In FIG. 8, a transducer assembly 140 includes a first tubular transducer 142 and a second tubular transducer 144, where the outermost ends of the transducers are secured within a cavity 146 formed in catheter body 148. Catheter body 148 further includes a central lumen 150 and a fluid infusion lumen 152. An interface member 154 having a circumferential flange 156 is mounted over the transducers 142 and 144 in a manner such that the flange 156 is captured between the inner ends of the transducers. The transducers 142 and 144 will be wired so that they oscillate longitudinally in the same direction, but 180° out of phase. In this way, the outer ends of the transducers 142 and 144 will remain fixed within the catheter body 148, while their inner ends oscillate longitudinally, driving the interface member 154. In this way, a cylindrical interface surface 158 on the exterior of interface member 154 will be longitudinally oscillated according to the method of the present invention.

A further alternative transducer assembly 200 is illustrated in FIG. 9. Catheter body 202 comprises a central lumen 204 and a pair of tubular transducers 206 and 208. Transducers 206 and 208 are captured within a recess in the catheter body 202, in a manner analogous to that illustrated in FIG. 8, so that a protruding flange member 210 is oscillated longitudinally when the transducers are activated. The flange 210, in turn, projects outwardly into a fluid region surrounding the catheter body 202 so that the flange can circulate fluid, as illustrated by circulation lines 211. The catheter body 202 further includes a pair of inflatable balloons 216 and 218 usually elastomeric balloons formed of silicone rubber, latex, or the like. By inflation of these balloons 216 and 218, as shown in broken line, a region 220 surrounding the catheter body and within the lumen of the body vessel V is created. Usually, the catheter will be provided with a fluid infusion lumen (not shown) which is disposed to release infusate into the region between the balloons 216 and 218.

Figure 10:
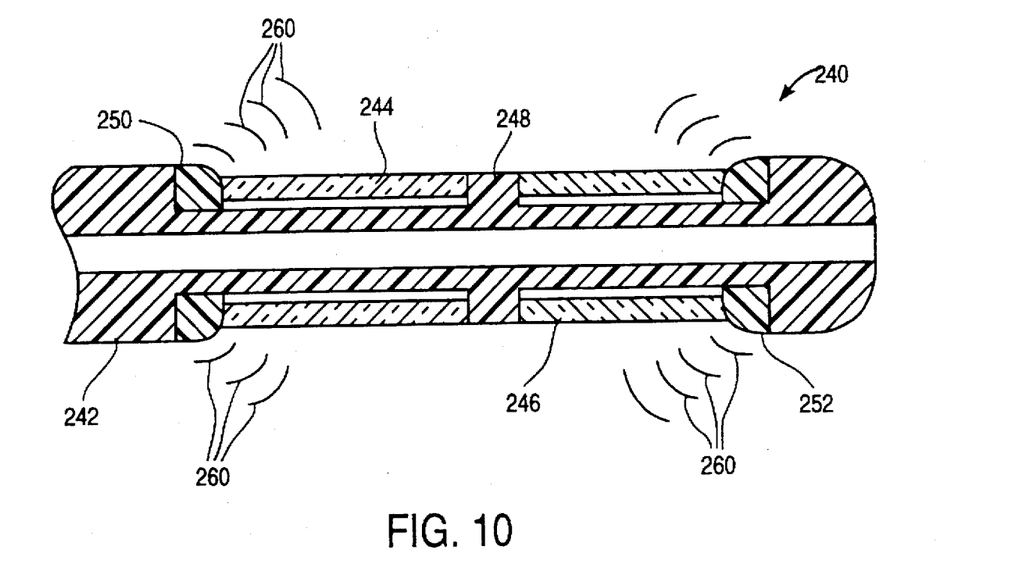
FIG. 10 is a detailed view of the distal end of a still further catheter constructed in accordance with the principles of the present invention, shown in cross-section.

A still further alternative transducer assembly 240 is illustrated in FIG. 10. The transducer assembly 240 is at the distal end of catheter body 242 and includes a first tubular transducer 244 and a second tubular transducer 246 received on the proximal and distal sides, respectively, of a flange 248 which is fixed relative to the catheter body 242. A first resilient bumper 250 is disposed at the proximal end of the first tubular transducer 244 and a second resilient bumper 252 is disposed at the distal end of the second tubular transducer 246. The tubular transducers 244 and 246 are connected to oscillate in an out-of-phase manner, as described previously. Thus, the motion will be absorbed by the bumpers 250 and 252, causing said bumpers to oscillate. The oscillating bumpers, in turn, will radiate ultrasonic energy into the medium surrounding the catheter body 242, as illustrated by wavefront lines 260, creating standing waves which will have a shearing effect on the vascular wall. Alternatively, the two transducers might be driven at different frequencies so as to create travelling shear waves at the vascular wall.

Although not specifically shown in FIGS. 7-10, it is to be understood that the distal end of the catheter supporting the transducer elements and the interface member will usually be fabricated from a rigid material, typically stainless steel with a Rockwell hardness of 35. The method of assembly (not shown) shall include conventional catheter assembly techniques to include but not be limited to joining by threaded shafts and tubes, joining by bonding means such as welding, soldering, and adhesives such as epoxies, to name but a few.

Figure 11:
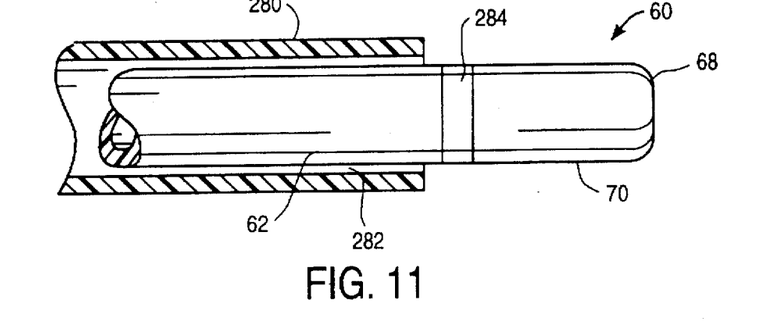
FIGS. 11–13 illustrate modifications of the external surface of various interface members which may be incorporated in the various catheters of the present invention.

Referring now to FIG. 11, the transducer assembly 60 of FIG. 5 is illustrated inside of a coaxial sheath 280. The sheath defines an annular lumen 282 which is suitable for delivering fluid agents to the region of the cylindrical interface surface 70. Optionally, a resilient ring 284 is mounted in the space between the proximal end of the interface member 68 and the distal end of catheter body 62. The ring member 284 is thus able to seal the catheter so that fluid is inhibited from entering into the region of the transducer 64.

Other modifications of the catheters of the present invention may be made in order to facilitate the delivery of the liquid therapeutic or other agent. For example, in the embodiment of FIG. 5, a fluid injection port could be provided immediately proximal to the proximal end of the cylindrical interface surface 70. On proximal displacement of the interface member 68, fluid leaving the port would be compressed and forced to flow radially outward from the catheter. On distal displacement of the interface member 68, a vacuum would be drawn over the fluid outlet port, drawing fluid from the central lumen. In this way, driving of the interface member 68 could act partially as a pump to withdraw fluid from the catheter.

Figure 12:
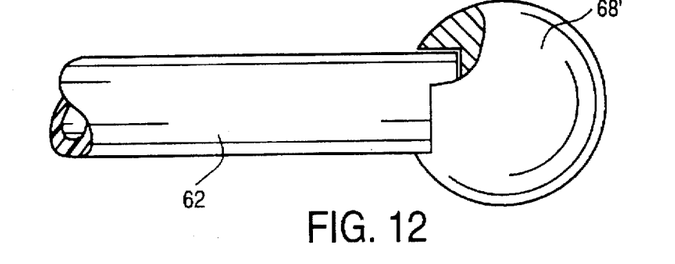

Referring now to FIG. 12, a catheter similar to that illustrated in FIG. 5 is illustrated, except that an interface member 68' has a generally spherical geometry. Such a spherical interface member provides an interface surface capable of radiating ultrasonic energy in a generally spherical pattern. In addition to its acoustic properties, such a tip geometry is less traumatic to the vascular wall.

Figure 13:
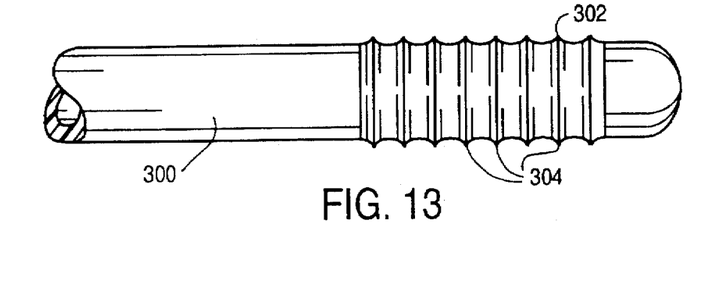

Referring now to FIG. 13, a catheter 300 has a cylindrical interface surface 302 with an irregular surface. In particular, the surface irregularities comprise a series of circumferential ridges 304 axially spaced-apart along the length of the surface. Such surface irregularities can enhance the transfer of oscillatory motion from the catheter surface into fluids surrounding the catheter 300.

Although the foregoing invention has been described in some detail by way of illustration and example, for purposes of clarity of understanding, it will be obvious that certain changes and modifications may be practiced within the scope of the appended claims.

What is claimed is:

1. A catheter comprising:
   a catheter body having a proximal end and a distal end;
   an oscillating driver disposed in catheter body; and
   an interface member having an interface surface which extends axially over at least a portion of and is spaced-apart from a circumferential surface of the catheter body, wherein the interface member is coupled to the oscillating driver at a single location so that said driver will transmit axial oscillations to the interface member to cause the interface surface to axially oscillate as a single body relative to the catheter body to induce transverse wave motion in fluid lying adjacent to the catheter body.

2. A catheter as in claim 1, wherein the interface surface further includes a portion which extends laterally over a distal end of the catheter.

3. A catheter as in claim 1, wherein the interface surface consists essentially of the portion which extends axially over the circumferential surface of the catheter body.

4. A catheter as in claim 1, wherein the catheter body further has a lumen for delivering fluid agents from the proximal end to near the interface member.

5. A catheter as in claim 1, further comprising a sheath disposed coaxially over the catheter body, which sheath defines a fluid infusion lumen for delivering fluid agents from the proximal end to near the interface member.

6. A catheter as in claim 1, wherein the oscillating driver comprises a longitudinally oscillating member and a spring element, wherein the interface member is connected at a proximal end to the catheter body and at a distal end to the interface member, wherein the longitudinally oscillating member is disposed between the catheter body and the interface member, and wherein the mass of the interface member, and elastic modulus of the spring member and of the longitudinally oscillating member are selected to provide resonant operation at a preselected drive frequency.

7. A catheter as in claim 6, wherein the resonant operation is at a frequency in the range from 10 kHz to 300 kHz.

8. A catheter as in claim 1, further comprising expansible members disposed proximally and distally of the interface surface and a lumen for delivering fluid agents to a location between said expansible members.

9. A catheter comprising:
   a catheter body having a proximal end and a distal end;
   a longitudinally oscillating driver having a proximal end and a distal end, said driver extending distally from the distal end of the catheter body; and
   an interface member spaced-apart from the catheter body and coupled to the distal end of the longitudinally oscillating driver at a single location, said interface member having an interface surface at least a portion of which is disposed circumferentially about the catheter body.

10. A catheter as in claim 9, wherein the interface surface includes both a lateral portion and a circumferential portion.

11. A catheter as in claim 10, wherein the lateral portion is flat.

12. A catheter as in claim 10, wherein the lateral portion is convex.

13. A catheter as in claim 10, wherein at least a portion of the circumferential portion has surface irregularities to enhance mixing of fluid adjacent to the surface.

14. A catheter as in claim 9, wherein the longitudinally oscillating driver comprises a longitudinally oscillating member and a spring element connecting the interface member to the catheter body, wherein the interface member engages distal ends of the spring element and of the oscillating driver.

15. A catheter as in claim 14, wherein the oscillating driver comprises a longitudinally oscillating member selected from the group consisting of piezoelectric elements and magnetostrictive elements.

16. A catheter as in claim 15, wherein the longitudinally oscillating member comprises a tubular piezoelectric transducer having an inner cylindrical electrode and an outer cylindrical electrode.

17. A catheter as in claim 16, wherein the tubular piezoelectric transducer oscillates at a frequency in the range from 10 kHz to 300 kHz.

18. A catheter as in claim 15, wherein the longitudinally oscillating member comprises a piezoelectric stack including a plurality of ceramic disks having electrodes therebetween.

19. A catheter as in claim 18, wherein the piezoelectric stack oscillates at a frequency in the range from 10 kHz to 300 kHz.

20. A catheter as in claim 14, wherein the interface member has a mass in the range from 0.3 gm to 4 gm.

21. A catheter as in claim 14, wherein the spring element comprises at least one rod secured at a proximal end to the catheter and/or tail mass and at a distal end to the interface member.

22. A catheter as in claim 21, wherein the spring element consists of a single rod disposed coaxially within the catheter.

23. A catheter as in claim 21, wherein the spring element comprises at least two parallel rod members disposed symmetrically about the axis of the catheter body.

24. A catheter as in claim 9, further comprising expansible members disposed proximally and distally of the interface surface and a lumen for delivering fluid agents to a location between said expansible members.

25. A catheter comprising:
    a catheter body having a proximal end and a distal end;
    an interface member having an interface surface; and
    a pair of longitudinally oscillating drivers connected in tandem so that the combined lengths of the drivers remains substantially constant as the drivers are oscillated;
    wherein the interface member is mechanically coupled to the catheter body through the pair of drivers so that simultaneous oscillation of the drivers induces longitudinal movement of the interface surface.

26. A catheter as in claim 25, wherein a distal end of the distal-most driver and a proximal end of the proximal-most driver are fixed relative to the catheter body and the interface member is secured to a location between the drivers.

27. A catheter as in claim 25, wherein a location between the drivers is fixed relative to the catheter body and the interface member is secured to a distal end of the distal-most driver and to a proximal end of the proximal-most driver.

28. A catheter as in claim 25, wherein the interface surface is generally cylindrical.

29. A catheter as in claim 28, wherein the cylindrical interface surface has a length in the range from 6 mm to 30 mm and an outer diameter in the range from 2 mm to 5 mm.

30. A catheter as in claim 29, wherein the cylindrical interface surface is smooth.

31. A catheter as in claim 29, wherein the cylindrical interface surface is irregular.

32. A catheter as in claim 25, wherein the interface member comprises an annular flange that is disposed circumferentially about the catheter body.

33. A catheter as in claim 25, wherein the catheter body further has a lumen for delivery of fluid agents from the proximal end to a location near the interface surface.

34. A catheter as in claim 25, further comprising a sheath disposed coaxially over the catheter body, which sheath defines a fluid infusion lumen for delivering fluid agents from the proximal end to near the interface surface.

35. A catheter as in claim 25, further comprising expansible members disposed proximally and distally of the interface surface and a lumen for delivering fluid agents to a location between said expansible members.

36. A catheter as in claim 25, wherein the longitudinally oscillating drivers each comprise a longitudinally oscillating member selected from the group consisting of piezoelectric elements and magnetostrictive elements.

37. A catheter as in claim 36, wherein the longitudinally oscillating members comprise a hollow piezoelectric cylinder having an inner cylindrical electrode and an outer cylindrical electrode.

38. A catheter as in claim 37, wherein piezoelectric cylinder has dimensions and is composed of a material which in combination with the other components of the catheter provide oscillation at a frequency in the range from 10 kHz to 300 kHz.

39. A catheter as in claim 36, wherein the longitudinally oscillating member comprises a plurality of ceramic disks having electrodes therebetween.

40. A catheter as in claim 25, wherein the pair of longitudinally oscillating drivers are suspended in a resonant mass assembly near the distal end of the catheter body.

41. A catheter as in claim 40, wherein the resonant mass assembly comprises an interface member, a tail mass, and a spring member extending between the interface member and the tail mass, wherein the longitudinally oscillating drivers are disposed between the interface member and the tail mass.

42. A method for treating an intraluminal site, said method comprising:

providing a catheter having an interface member near its distal end;

advancing a circumferential interface surface on the catheter to a region near the intraluminal site; and driving the interface surface in an axial direction relative to the catheter to induce wave motion in fluid adjacent to the circumferential interface surface, wherein all points along the length of the interface surface move in unison.

43. A method as in claim 42, wherein the intraluminal lesion is a vascular angioplasty treatment site.

44. A method as in claim 42, wherein the interface member is driven at a frequency in the range from about 10 kHz to 300 kHz.

45. A method as in claim 44, wherein the interface member is driven to a longitudinal amplitude in the range from 0.05 µm to 20 µm.

46. A method as in claim 42, wherein the circumferential surface is cylindrical having a length in the range from 6 mm to 30 mm and a diameter in the range from 2 mm to 5 mm.

47. A method as in claim 42, further comprising delivering a therapeutic agent through the catheter to the intraluminal lesion.

48. A method as in claim 47, wherein the therapeutic agent is delivered while ultrasonic energy is being radiated into the region.

49. A method as in claim 47, wherein the interface member surface is engaged against a vascular obstruction.

50. A method as in claim 47, wherein the therapeutic agent is a fibrinolytic agent delivered to a vascular stenosis to treat clot.

51. A method as in claim 47, wherein the therapeutic agent is an anti-thrombotic agent delivered to a previously treated vascular site to inhibit restenosis.

52. A method as in claim 47, further comprising isolating a region surrounding the circumferential interface surface while driving the interface surface.

53. A method as in claim 52, wherein the isolating step comprises expanding a pair of expansible members on the proximal and distal sites of the circumferential interface surface, wherein said expanded expansible members seal against the luminal wall.

* * * * *